United States Patent [19]

Shank

[11] B 4,001,480

[45] Jan. 4, 1977

[54] ENCAPSULATION PROCESS UTILIZING MICROORGANISMS AND PRODUCTS PRODUCED THEREBY

[75] Inventor: Joseph L. Shank, Matteson, Ill.

[73] Assignee: Swift & Company, Chicago, Ill.

[22] Filed: Aug. 16, 1974

[21] Appl. No.: 498,208

[44] Published under the second Trial Voluntary Protest Program on April 13, 1976 as document No. B 498,208.

[52] U.S. Cl. ............................. 428/411; 195/56; 195/98; 195/57; 195/81; 195/1; 426/61; 426/62; 426/96; 426/98; 426/650; 426/651; 252/316; 424/93; 424/16

[51] Int. Cl.² .................. B41M 5/02; C12D 13/08

[58] Field of Search ............. 195/56, 57, 59, 1, 98, 195/81; 424/93, 92; 252/316; 117/36.2; 161/DIG. 5; 426/96, 98; 428/411

[56] References Cited

UNITED STATES PATENTS

| | | | |
|---|---|---|---|
| 2,346,011 | 4/1944 | Damm | 195/81 |
| 3,137,631 | 6/1964 | Soloway | 426/98 |
| 3,151,038 | 9/1964 | Gray | 195/81 |
| 3,418,250 | 12/1968 | Vassiliades | 252/316 |
| 3,681,199 | 8/1972 | Rokitansky | 195/98 |
| 3,743,579 | 7/1973 | Zilberblat | 195/104 |
| 3,779,869 | 12/1973 | Zienty | 195/56 |
| 3,834,991 | 9/1974 | Megraw et al. | 195/59 |
| 3,860,490 | 1/1975 | Guttag | 195/56 |

OTHER PUBLICATIONS

Microbiology, by Pelczar et al., p. 151, McGraw-Hill Book Co., 1958.

*Primary Examiner*—Alvin E. Tanenholtz
*Attorney, Agent, or Firm*—Edward T. McCabe; Charles E. Bouton; Raymond M. Mehler

[57] ABSTRACT

Substances such as dyes, drugs, condiments, flavors, aromas, chemicals, vitamins, adhesives, and the like are provided as encapsulated within the cells of microorganisms. Microorganisms such as yeasts, fungi, molds, and protozoa are grown in a medium so as to promote the formation of biological capsules, such as by forming relatively large globules of fat within the cell wall. A substance such as a dye, a drug, a condiment, a flavor, an aroma, a chemical, a vitamin, an adhesive, and the like is passed through the cell wall of the microorganism and into the biological capsule thereby producing an encapsulated product.

20 Claims, No Drawings

ENCAPSULATION PROCESS UTILIZING MICROORGANISMS AND PRODUCTS PRODUCED THEREBY

This invention relates to encapsulated products. More particularly, the present invention refers to any number of substances encapsulated or microencapsulated within biologically produced capsules and a process for preparing same.

Techniques identified by the term "microencapsulation" origninated in connection with so-called carbonless carbon paper, where leuco dyes are encapsulated in a gelatin-gum arabic system through a coacervation process. Generally, coacervation refers to the salting out of a lyophilic sol into liquid droplets which serve as the microcapsules. The prior art describes that such coacervate microcapsules can be formed by using various colloidal systems, including the material to be encapsulated as one of the phases of the system. Second and third phases of these prior art colloidal systems include various combinations of a continuous phase and a coating phase, such as gelatin with gum arabic, polyetheleneimine with gum arabic, or gelatin with various synthetic anionic polymers. The current state of the art relative to teachings of microencapsulation through coacervation is exemplified by Wurzberg, et al., U.S. Pat. No. 3,499,962, wherein amylose is utilized in the continuous phase.

With prior art encapsulation procedures, such as coacervation, it is necessary to proceed with critical and sensitive steps, including at least some of the following: precise dilution of the colloidal system, carefully regulated stirring, pH and/or temperature adjustments to form a preliminary film through electrostatic attraction and solubility changes, specialized centrifuging or spraying, and gelling of the coating material. Known encapsulation techniques are not only tedious and exacting, but they are also high in cost. Prior art microencapsulation may increase the cost of some final products by as much as 10 to 20%.

I have discovered that encapsulation can be carried out in a manner that is less expensive and less exacting than that required by prior art encapsulation, such as through coacervation techniques.

It is accordingly an object of the present invention to provide a product that is a substance such as a dye, a drug, a condiment, a flavor, an aroma, a chemical, a vitamin, an adhesive, or the like, encapsulated within biological capsules naturally provided by microorganisms such as fungi, yeasts, and protozoa.

A further object is to provide a product that has a biological casing around a liquid product thereby giving the appearance that the liquid product is a solid, a granule, or a powder.

Another object of this invention is to have a product in which noxious or penetrating odors are confined within capsules until it is desired that they be released.

One other object is to provide biological capsule products containing two or more different components that, were they not encapuslated, would react with each other.

An additional object of this invention is a process for growing biological entities, often under conditions of growth to produce excessive fat globules, and introducing thereinto any number of various fat soluble products, such as dyes, drugs, condiments, flavors, aromas, chemicals, vitamins, adhesives, or the like.

Still another object of the present invention is a process for the preparation of a so-called carbonless carbon paper by casting onto treated paper biological capsules into which have been encapsulated a lueco dye.

The product of the present invention is a microcapsule of any one of a variety of substances that one might desire to place into encapsulated form, which substances are fat soluble and/or are permeable through protozoa membrane. By the present process, these substances are encapsulated within a biological capsule to form an encapsulated product.

Other objects, if not set forth specifically herein, will be readily apparent to those skilled in the art from the following detailed description.

I have determined that microorganisms can provide an encapsulation means that is suitable for the encapsulation or microencapsulation of any substance that is fat soluble and thus that can be absorbed into fat containing cells of microorganisms such as yeast or fungi. Suitable capsules may also be prepared in accordance with my invention by utilizing protozoa, which will permit the encapsulation of not only fat soluble substances, but also additional substances that are permeable through protozoa membranes but that might not be fat soluble.

The present product is a substance that has been absorbed into fat globules of fungi including yeasts and molds that are either living or dead or that has been ingested by a living protozoa or that has been absorbed into a non-living protozoa. The protozoa or the fat globules of the yeasts or fungi provide a biological capsule containing the substance.

Any microorganism that synthesizes fat within itself, such as yeasts, molds, or other fungi, are suitable for producing the cells into which the substances to be encapsulated may be absorbed. Examples of such fungi include *Torulopsis lipofera, Endomyces vernalis, Rhodotorula agracuis, Oospera lactis, Saccharomyces cerevisiae* ("baker's yeast"), *Candida reukaufii, Oospera walbroth, Rhodotorula glutinis, Rhodotorula gracilis, Lycogala epidendrum, Penicillium javanicium, Aspergillus sydowi, Claviceps purpurea, Fusarium lini, Rhizopus oligosporus, Mortierella pusilla, Mucor racemosus,* and the spores of ferns such as *Lycopodium clavatum*. Any relatively large protozoa also may be utilized, examples of such protozoa being those found in the rumen, including *Bacteriodes succinogenes, Etidinium ecaudatum, Entodinium caudatum, Eudipolodinium neglectum, Eudiplodinium maggii, Diplodinium dentatum,* and *Polyplastron multivesiculatum*.

Among the numerous substances that may be absorbed into and encapsulated within the fat globules of the yeasts, molds, or other fungi, or within protozoa are various dyes. Of particular commercial importance are leuco dyes that are especially suitable for "carbonless" carbon paper applications. These dyes include the arylmethane dye lactones, such as crystal violet lacton, triarylmethane dye derivatives, and dye derivatives of bis (p-dialkylaminoaryl) methane. Specific examples of the chemical formulas of these last-listed dyes are as follows:

1-[bis (p-dimethylaminophenyl)methyl]-pyrrolidine
1-[bis(p-dimethylaminophenyl)methyl]-piperidine
1-[bis(p-diethylaminophenyl)methyl]-piperidine
4-[bis(p-dimethylaminophenyl)methyl]-morpholine
4-[bis(p-diethylaminophenyl)methyl]-morpholine
1-[bis(p-dimethylaminophenyl)methyl]-piperazine 1-[bis-(p-dimethylaminophenyl)methyl]-4-methylpiperazine
1-[bis(p-dimethylaminophenyl)methyl]-4-hydroxyethylpiperazine
1,4-bis[bis(p-dimethylaminophenyl)methyl]-piperazine
1,4-bis[bis(p-diethylaminophenyl)methyl]-piperazine
1-[bis(p-dimethylaminophenyl)methyl]-benzotriazole
1-[bis(p-dimethylaminophenyl)methyl]-3,5-dimethylpyrazole
1-[bis(p-dimethylaminophenyl)methyl]-benzimidazole
N-[bis-(p-dimethylaminophenyl)methyl]-indole
N-[bis-(p-dimethylaminophenyl)methyl]-pyrrole
1-[bis(p-dimethylaminophenyl)methyl]-2-methyl-2-imidazoline
N-[bis(p-dimethylaminophenyl)methyl]-carbazole In addition to such dyes, any substance that is fat soluble or permeable through the cell wall of protozoa can be encapsulated in accordance with the present invention. Such substances may be drugs such as analgesics, antipyretics, decongestants, and the like, for example, malathion, phenylbutazone, caffeine, aspirin, etc. Also capable of encapsulation in accordance with the present invention are various fat soluble condiments, flavors and aromas, including essential oils and flavors, citric acid, and the like. The present invention is likewise used in connection with any fat-soluble vitamin as the encapsulated substance, thereby prolonging the potency thereof. Especially suitable are Vitamin A and Vitamin E. Vitamin $D_2$, Vitamin $D_3$, Vitamin $D_4$, and Vitamin $K_1$ are among other vitamins that may be encapsulated in accordance with the present invention.

Also any chemical that is fat soluble and capable of passing through the fungi or yeast cell wall or through the cell wall of the various protozoa may be utilized as substances that are encapsulated. Such chemicals include, but are not limited to kerosene, soybeam oil, ethyl phthalate, perchloroethylene, xylene, formamide, and zinc chromate.

Any number of various lubricants are also capable of being utilized as the encapsulated substance. Utilization of the present invention for storing different substances that react with each other is exemplified by packaging as one item an encapsulated epoxy adhesive and an encapsulated curing agent. The adhesive can then be activated by mixing together and rupturing the capsules to thereby place the adhesive into contact with the curing agent.

The biological capsules themselves may, if desired, be either hardened or softened, depending upon whether the final encapsulated product is to be easily rupturable or especially resistant to permitting escape of the substance from out of the biological capsule. The final product may be in the nature of an accumulation of free-standing encapsulated particles that combine to give the appearance of a powder or a granular substance. Alternatively, the final product may consist of a cluster or colony of encapsulated products which are free-standing. This cluster or colony form can be particularly suitable for products that are to be of the "time-release" type in that the outer cells of the colonies will rupture sooner that the cells in the interior of the colonies. By "time-release" is meant that the encapsulated substance will tend to escape from the microcapsules over an extended period of time. This aspect can also be achieved by including in a single marketed product capsules that have cells walls of varying thicknesses or that have been softened or hardened to various and different degrees.

Also, the final product may be such that the individual capsules or clusters of capsules are not free-standing, but are utilized to form a covering film upon a web of any suitable mounting medium, including, but not limited to, paper, cloth, synthetic materials, metallic films, and the like.

This latter form of the final product includes carbonless carbon paper, wherein the fat globules or protozoa contain a leuco dye and are cast upon a web of material that had been previously coated with a clay consistent with prior art teachings. This clay is one that had been acidified by treatment with an organic or mineral acid, or the clay could have been treated with alkali, depending upon the particular pH characteristics of the specific leuco dye utilized. When pressure is applied to this treated web of material, the biological capsules subjected to such pressure burst, permitting the leuco dye to come into contact with the treated paper, at which time the leuco dye undergoes a pH change, thereby effecting transformation of the dye from its colorless state to its visible color state.

When the process of the present invention utilizes a fungi such as a mold or a yeast in forming the biological capsule, same is grown under conditions particularly suitable for enhancing a growth of fat cells therein. A normally grown cell will have a certain amount of fat; however, when dried for use as a microcapsule, a normally grown cell becomes quite hard and a considerable amount of pressure is needed to break the cell wall. However, if a cell contains a substantial proportion of fat, the toughness of the cell wall can be more easily varied to achieve a desired ease of rupture of the cell wall.

Generally, growth of excess fat is achieved by nurturing the fungi in a medium that is poor in nitrogen, whereupon there will be provided a growth pattern that will produce up to 40 to 60 percent fat by weight. This fat can be seen under a microscope as a large, glistening globule occupying the greater portion of the cytoplasm.

For example, the yeast *Endomyces vernalis* produces about 42% fat by weight when grown under proper conditions. Such known growth conditions include the preliminary step of growing this yeast for two or three days at 15°–20°C. on a medium relatively rich in nitrogen and poor in carbohydrates. Then, the medium is changed to one that is very high in carbohydrate content and very low in nitrogen content. AFter about seven or eight days, this yeast assimilates most of the carbohydrates, thereby becoming very rich in fat.

Large fat globules can also be obtained by growing yeasts belonging to the *Lipomyces* genus in nitrogen-deficient media and in the presence of carbon sources such as ethanol, glycerol, or lactose.

Internal fat production in yeasts can also be enhanced by including calcium in the nutrient medium. It is also believed that the addition of phosphates to the nutrient medium can also increase fat storage. Aeration of molds and yeasts in suspension generally aids in the formation of excess fat.

Another example of excess fat production is the growing of the yeast *Rhodotorula gracilis* rapidly in a normal nutrient medium for about ten hours, after which the medium is changed to substantially all sugar for a time period of about fifty hours. The final fat content is approximately 60% by weight.

When protozoa are utilized as the biological capsules, it is possible to encapsulate any substance that is ingested into the protozoa while still living. Also, dead protozoa may be utilized as the biological capsule, whereby any substance absorbed through the protozoa membrane is encapsulated.

In order to complete the encapsulation process, the substance to be encapsulated is placed into contact with the fungi cells containing excess fat, or with the protozoa. Generally, the yeasts, molds, or other fungi, or protozoa will be dead at this stage. However, it is also possible to achieve the encapsulation while the fungi or protozoa are still living; of course, if the substance being encapsulated is toxic to the particular fungi or protozoa, same will die during the encapsulation process. The substance and the cell being in contact, the substance permeates through the cell wall and is introduced into the cell. The mechanism for such introduction is thought to be primarily dependent upon diffusion gradients and the difference in the concentrations of the substance outside of and within the cell. Although not an essential feature of the invention, the encapsulation process can be enchanced somewhat by the application of physcial pressure directed toward the cell. A further optional means to enchance the encapsulation process is by warming during encapsulation. Such heating can speed up the process.

Often, after encapsulation is completed, and the product dried, the cell wall is so tough that it is difficult to burst the capsules. If it is desired to have softer capsules, the encapsulated product can next be treated with protoelytic enzymes. For example, alkaline protease on the order of ½ to 1 percent basis weight to cell protein will effectively soften most cell walls to make them less resistant to rupture. Such softening can also be useful to promote encapsulation. For this latter purpose, the softening step is carried out before the substance is introduced within the biological capsule.

On other occasions, when some substances are encapsulated into certain biological capsules in accordance with the process of the present invention, it is useful to thereafter harden the cell wall, thereby preventing premature rupture of the capsules which would liberate the substance before it is desired to do so. Generally, substances such as dilute aldehydes act as suitable hardening agents. Dilute aldehydes react with protein in the cell wall to promote cross-linking in the cell wall. Found to be especially suitable for this purpose are gluteraldehyde, formaldehyde, and osmium tetroxide.

The following examples are presented to illustrate the invention. It will be understood that the specific embodiments and illustrations should not be taken in any manner as limiting the invention as defined in the appended claims. Obviously many modifications and variations of the invention as set forth herein may be made without departing from the spirit and scope thereof.

EXAMPLE I

The yeast *Torulopsis lipofera* is placed within a nutrient medium that is low in nitrogen content, also having a high carbohydrate content. The yeast is permitted to grow until approximately 50% by weight of the cell is fat. This volume of fat is identified under a microscope as a large glistening globule occupying a substantial portion of the cytoplasm of the grown yeast. Crystal violet lacton, a leuco dye, is then put into solution with ethyl alcohol and placed into contact with this high fat content yeast for several minutes or until the cells are observed as being infused with the dye.

The dyed cells are then harvested by centrifugation. Thereafter, the cells are resuspended in an alcoholic solution as a slurry and then cast upon a paper, utilizing a small quantity of a 10% starch-solution adhesive. This paper is previously treated with a suitable clay that is acidified with a mineral acid. Thus prepared is a so-called carbonless carbon paper. When pressure is applied to this product, for example by a pen or a typewriter character, the pressure crushes the cells which in turn releases the leuco dye so that it comes into contact with the carrier paper treated with the acid clay, thereby transforming the dye from its colorless state to its violet color. The dye's coming into contact with the acidified clay causes a pH change of the dye which effects the color change.

EXAMPLE II

The yeast *Endomyces vernalis* is used to prepare a carbonless carbon paper in the manner of Example I except that here the slurry is warmed to 130°F. to promote passage of the dye through the cell membrane. Also, the dye used is leuco methylene blue, which is dissolved in an alcoholic solution of water and ethyl alcohol, and the harvesting is accomplished by filtration rather than by centrifugation. Since this encapsulated product is not readily rupturable, the final product is treated with a proteolytic enzyme softening agent. The cells are then ruptured and color formation is observed.

EXAMPLE III

Sodium sulfite is encapsulated within a yeast in accordance with Example I and cast upon a web of paper treated with lead acetate. These cells are ruptured with a rod to produce a permanent black marking upon the web at the locations to which the rod was moved.

EXAMPLE IV

Baker's yeast, *Saccharomyces cerevisiae*, grown to enhance fat deposition within the cell, is infused with oil of wintergreen (methyl salicylate) in a manner similar to that of Example I, harvested by filtration, washed and dried. Upon crushing the cells, a marked odor of wintergreen is observed.

EXAMPLE V

Acetylsalicylic acid (aspirin), an acetyl derivative of methyl salicylate, is encapsulated in accordance with Example IV. The final product is an aspirin formulation in which the aspirin is not released until the yeast cell has been digested.

I claim:

1. An encapsulation process comprising the steps of: growing a fungus under conditions that produce a fungus having a fat content of about 40 to 60% by weight, passing a fat-soluble substance into the fat within the grown fungus by placing said fungus into contiguous contact with said substance to thereby encapsulate said substance, said fat-soluble substance being passively retained within said fat and not being a natural constituent of the fungus; and harvesting said encapsulated substance.

2. The process of claim 1, wherein the growing step is accomplished within a nutrient medium that is relatively low in nitrogen content and relatively high in carbohydrate content to enhance the formation of fat within the fungus.

3. The process of claim 1, wherein the fat-soluble substance is a dye, a lubricant, a flavor, an aroma, or an adhesive.

4. The process of claim 1, further including the step of casting the harvested encapsulated substance onto a web of treated material.

5. The process of claim 4, wherein the casting is accomplished with an adhesive, the web is treated with an acidified clay, and the substance is a leuco dye that is initially colorless and exhibits a color when the pH thereof is lowered upon coming into contact with said acidified clay.

6. The process of claim 1, including the additional step of softening the fungus capsule by placing said encapsulated substance into contact with a proteolytic enzyme, said softening step being accomplished after the harvesting step.

7. The process of claim 1, including the additional step of softening the fungus by placing same into contact with a proteolytic enzyme, said softening step being accomplished prior to the substance passing step.

8. The process of claim 1, including the additional step of hardening the fungus capsule by placing same into contact with a dilute aldehyde, said hardening step being accomplished after the harvesting step.

9. The process of claim 1, wherein the substance passing step includes heating to promote passage of the substance into the fungus.

10. The process of claim 1, wherein the substance passing step includes applying physcial pressure to the substance and fungus in contiguous contact therewith to promote passage of the substance through the cell walls.

11. An encapsulation process comprising the steps of: growing a fungus in a nutrient medium that is nitrogen deficient to thereby enhance fat formation within the fungus so that the fungus has a fat content of about 40 to 60% by weight, passing a fat-soluble substance through the grown fungus and into the fat cells thereof by placing said fungus into contact with said substance to thereby encapsulate said substance, said fat-soluble substance being passively retained within said fat an not being a natural constituent of the fungus; softening the cell walls by placing the cells into contact with a proteolytic enzyme and harvesting the thus encapsulated substance.

12. An encapsulation process comprising the steps of: growing a fungus in a nutrient medium that is nitrogen deficient to thereby enhance fat formation within the fungus so that the fungus has a fat content of about 40 to 60% by weight; promoting encapsulation of a fat-soluble substance by passage thereof into the grown fungus by placing said fungus into contact with said substance and heating same, said fat-soluble substance being passively retained within said fat and not being a natural constituent of the fungus; and harvesting the thus encapsulated substance.

13. An encapsulated product comprising a capsule that is a fungus having a fat content of about 40 to 60% by weight, and a fat-soluble substance encapsulated and passively retained within said fat of the fungus, said fat solbule substance not being a natural constituent of the fungus.

14. The product of claim 13, wherein the fat-soluble substance is a dye, a lubricant, a flavor, an aroma or an adhesive.

15. The product of claim 13, further comprising a web of material onto which the substance encapsulated within the fungus has been cast.

16. The product of claim 15, wherein the substance is a leuco dye, and the web of material has been treated with an acidified clay.

17. The process of claim 1, wherein the fungus is an edible yeast, and the fat-soluble substance is a dye, a drug, a lubricant, a condiment, a flavor, an aroma, a vitamin, or an adhesive.

18. The process of claim 1, wherein said harvested, encapsulated substance is then washed and dried.

19. The product of claim 13, wherein the fungus is an edible yeast, and the fat soluble substance is a dye, a drug, a lubricant, a condiment, a flavor, an aroma, a vitamin or an adhesive.

20. The product of claim 15, wherein the substance is sodium sulfite, and the web of material has been treated with lead acetate.

* * * * *